Figure 1:
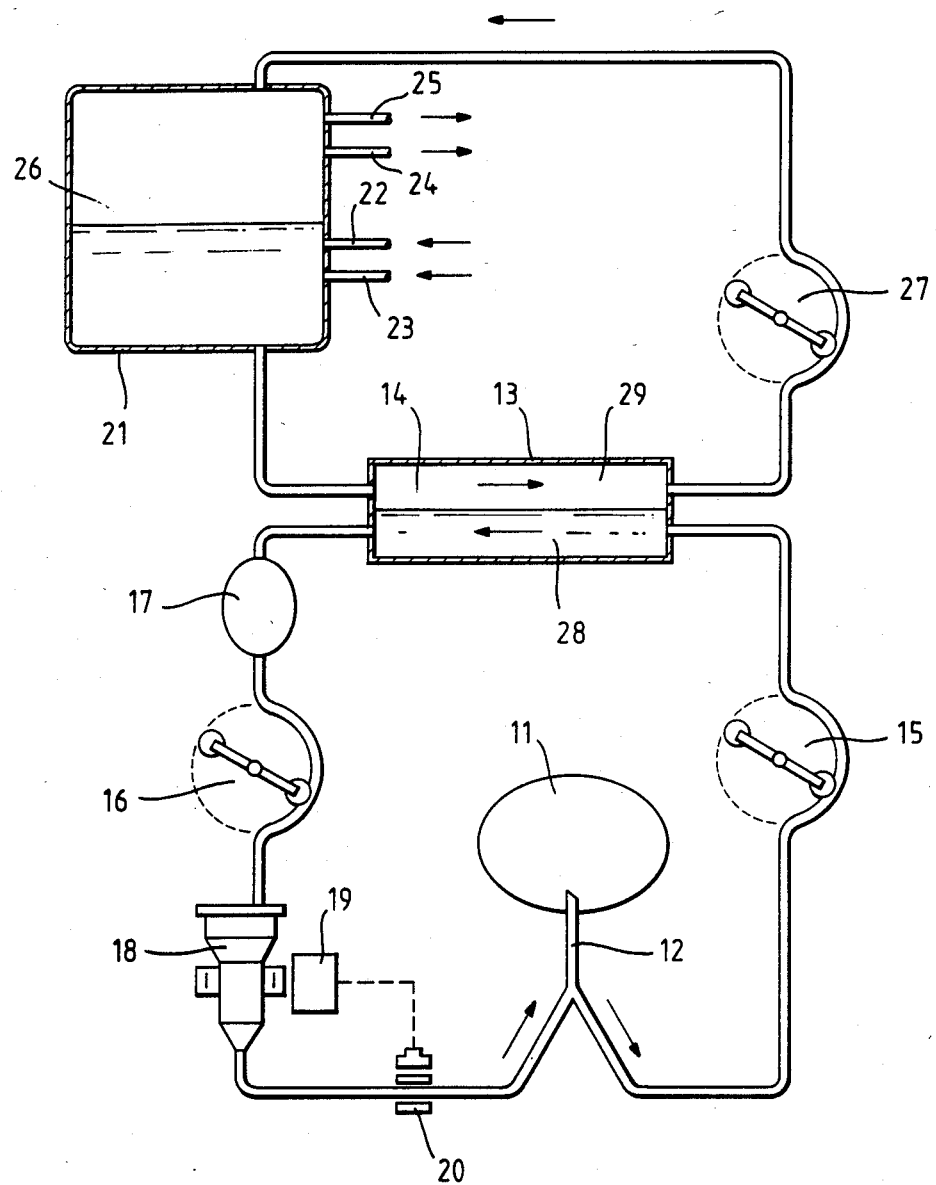

United States Patent [19]

Chevallet

[11] Patent Number: 4,599,165
[45] Date of Patent: Jul. 8, 1986

[54] SINGLE-NEEDLE ARTIFICIAL KIDNEY

[75] Inventor: Jacques Chevallet, Serezin du Rhone, France

[73] Assignee: Hospal Industrie, Meyzieu, France

[21] Appl. No.: 691,492

[22] Filed: Jan. 14, 1985

[30] Foreign Application Priority Data

Jan. 18, 1984 [FR] France .................. 84 00932

[51] Int. Cl.⁴ .................. A61M 5/00; A61M 7/00; B01D 13/00
[52] U.S. Cl. .................. 210/87; 210/97; 210/321.3
[58] Field of Search .................. 210/321.3, 85, 87, 97

[56] References Cited

U.S. PATENT DOCUMENTS 3,830,234  8/1974  Kopp .................. 210/321.3
3,902,490  9/1975  Jacobsen et al. .................. 210/321.3
4,096,859  6/1978  Agarwal et al. .................. 210/321.3

Primary Examiner—Frank Sever
Attorney, Agent, or Firm—Gerald D. Sharkin; Robert S. Honor; Walter F. Jewell

[57] ABSTRACT

A single-needle artificial kidney comprising a haemodialyser divided by a semi-permeable membrane into first and second compartments, one of which forms part of an extracorporeal blood circuit including a blood circulation pump and a single needle for inserting into the patient and a dialysis liquid circuit including the second chamber and a dialysis liquid pump. The dialysis liquid circuit is provided with means for periodically modulating the flow rate of the dialysis liquid in the haemodialyser between minimum and maximum values, the flow rate of the dialysis liquid being produced by a sensing pulsations of the blood at frequencies less than one hertz and using these pulsations via a servo-control to effect changes in the dialysis liquid flow rate so that it reaches maximum and minimum values simultaneously with maximum and minimum of the blood flow rate.

9 Claims, 5 Drawing Figures

SINGLE-NEEDLE ARTIFICIAL KIDNEY

The present invention relates to improvements in artificial kidneys, incorporating an extracorporeal blood circuit connected to the arteriovenous network of a patient by a single access such as a needle or catheter which is Y- or T-shaped. The invention relates more especially to an artificial kidney, the extracorporeal blood circuit of which incorporates a haemodialyser positioned between two blood circulation pumps.

Artificial kidneys of this type are already known and have the advantage, relative to the traditional kidneys which are connected to the patients by two independent needles, of requiring only a single access to the patient's arteriovenous network at each treatment, resulting in considerably less traumatisation.

As is known, in single-needle artificial kidneys, the blood is passed through the single needle or passage alternately in one direction and then in the opposite direction, either from the patient to the extracorporeal circuit of from the circuit to the patient. As a result, in the haemodialyser, whatever devices are used for absorbing pulsations, the blood does not flow at a uniform rate, but at a flow rate which will be described herein as pulsed. If consideration is now given to the average flow rate of blood, for example to the flow rate per hour passing through a haemodialyser, and if the efficiency of dialysis, that is to say the removal, for example of urea or creatinine, is compared, at the same blood flow rate, a single needle artificial kidney is formed to remove approximately 4% less than a conventional double-needle artificial kidney all other factors being equal. Furthermore, this reduction in the amount removed becomes more pronounced as the average blood flow rate is increased, and higher flow rates are in keeping with current possibilities and trends.

A similar loss in the amount removed is also found if the dialysis liquid alone is subjected to a pulsed system instead of a uniform flow system, all other conditions being equal and, in particular, the blood flow rate then being maintained essentially uniform.

It seems therefore that the replacement of a uniform flow rate in a haemodialyser by a pulsed flow rate, whether in respect of the blood or the dialysis liquid, is prejudicial to the efficiency of the dialysis.

Now, according to the present invention, it was found quite surprisingly that it was possible to carry out treatments using single-needle artificial kidneys and to find conditions for improved efficiency, for example in relation to the removal of urea and creatinine, which could be as good as those obtained with conventional double-needle artificial kidneys, if means were employed which permitted simultaneous pulsing of both the blood and the dialysis liquid in the haemodialyser.

The main object of the present invention is therefore to propose a single-needle artificial kidney which does not show loss in the ability to remove unwanted material as compared to the ability of a conventional double-needle artificial kidney at comparable flow rates of blood and dialysis liquid, especially at high average blood flow rates.

Another subject of the present invention is to propose a single-needle artificial kidney, the operation of which is simple, economical, automatic and reliable.

Further objects of the present invention will emerge in the course of the description which follows.

According to the present invention there is provided an artificial kidney comprising a haemodialyser, a semipermeable membrane which can effect dialysis and ultrafiltration of the blood dividing said haemodialyser into first and second compartments, an extracorporeal blood circuit including said first compartment, a blood circulation pump and a single needle for insertion into the patient, a dialysis liquid circuit including said second compartment and a dialysis liquid pump, means in said dialysis liquid circuit for repeatedly modulating the flow rate of said dialysis liquid in said haemodialyser between minimum and maximum values, a sensor sensitive to the pulsations of the blood in said extracorporeal blood circuit at frequencies below 1 hertz, and a servo-control operable in response to said sensor to control said means periodically modulating the flow rate of the dialysis liquid as a function of said pulsations of the blood at frequencies below 1 hertz.

Thus, it has been found advantagous to replace a constant flow rate of the dialysis liquid flow rate modulated according to the flow sequences of the blood in the haemodialyser which are imposed by the use of the single needle. This can be effected by a servo-control device known per se, this device being connected to a sensor which is sensitive to the pulsations of the blood which are imposed by the use of the single needle. This sensor is situated in the extracorporeal blood circuit, preferably immediately adjacent to the haemodialyser.

By pulsation of the blood, there is here understood any relatively low frequency pulsation of less than one hertz and preferably any pulsation between 0.05 and 1 hertz. The blood pulsations generated by using the single needle are in fact advantagously between 0.1 and 0.4 hertz. According to the system used for regulating the operation of the blood circulation pumps, the frequency of these pulsations is either strictly constant, because it is prescribed, or most frequently substantially constant, depending on possible slight fluctuations in the variations of blood pressure which are measured in the extracorporeal blood circuit immediately adjacent to the haemodialyser.

It is observed that these pulsations which arise from the use of the single needle are of substantially lower frequency than those which arise from any other cause, such as the beating of the heart or pumping by diaphragm, piston or peristaltic pumps. It is also noted that the range of flow rates of blood pulsed, for example, by a peristaltic pump is only about ±5% around the mean flow rate, whereas the range of sequential flow rates of blood imposed by the use of the single needle is generally greater than ±30% around the mean flow rate in the haemodialyser, despite the use of a pulsation-absorbing device. The blood pulsations to which the present invention relates therefore differ fundamentally and unambiguously from other types of pulsations which may be encountered. The term pulsations has, however, been retained here because it has already been widely used in the various senses mentioned.

Using the invention, it has also been observed that better removal of unwanted material, that is to say greater efficiency in the exchange of materials across the membrane of the haemodialyser, are obtained when the flow rate of the dialysis liquid is modulated in phase with respect to the flow rate of the blood in the haemodialyser. The respective flow rates of the blood and the dialysis liquid are therefore preferably synchronised so that they simultaneously reach their maximum and then their minimum, and this continues periodically in the haemodialyser according to the sequence imposed on the blood flow by using the single needle.

The blood and the dialysis liquid can pass through the haemodialyser in concurrent or crossed current flow, but most frequently they pass through it in countercurrent flow.

The pressure across the membrane in the haemodialyser that is to say the difference in pressure at any moment on either side of the membrane in the compartments through which, respectively, the blood and the dialysis liquid pass, is not generally substantially affected by modulating the flow rate of the dialysis liquid according to the present invention. It is known in fact that the pressure across the membrane is responsible for the flow of ultrafiltrate which passes from the blood into the dialysis liquid. For example, the pressure across the membrane is not significantly modified in an artificial kidney having a dialysis circuit which is looped on itself and isolated from the atmosphere whereby the volume of the ultrafiltrate is prescribed.

As a result, in distinction to what might normally have been feared in haemodialysers of the flat membrane type, where the blood and the dialysis liquid flow in countercurrent in very thin films, the membrane in practice undergoes no distortion which could restrict the advance of the blood and dialysis liquid, at their maximum flow rates in opposite directions. Only the instantaneous flow rates, and hence the instantaneous speeds at which the dialysis liquid passes over the surface of the membrane, are significantly altered.

According to the invention, it has been observed that advantage is to be gained from modulating the flow rate of the dialysis liquid between two predetermined limiting values, a minimum value and a maximum value. These limiting values are to be chosen so that the minimum value is low enough for a substantial economy to be achieved in dialysis liquid, and the maximum value high enough for a distinctly improved exchange efficiency to be attained. The flow rate of the dialysis liquid in a single-needle artificial kidney can thus be modulated between limiting values, in practice, between 100 and 1000 ml/min and preferably between 200 and 800 ml/min. By way of example, it has been observed that limiting values of 300 and 700 ml/min are very suitable. These limiting values are associated with average flow rates of blood which are commonly obtained with a single-needle artificial kidney, for example generally between 200 and 400 ml/min. Although the modulation of the flow rate of dialysis liquid can be carried out as a function of time according to any known principle, it is advantageous to arrive promptly at the minimum and maximum flow rates and to maintain them substantially constant as long as possible.

In order that the invention will be more readily understood the following description is given, merely by way of example, reference being made to the accompanying drawings, in which:

FIG. 1 is a schematic view of one form of a single-needle type artificial kidney according to the known prior art; and FIGS. 2 to 5 are similar views of various embodiments of the artificial kidney according to the present invention.

For greater convenience, the equivalent components of the artificial kidneys shown in the various figures are designated by the same numbers.

Referring first to FIG. 1, blood is withdrawn from the patient 11 by means of a single access 12 of any type known per se, such as a needle or a catheter, which is Y-or T-shaped. The blood passes through an extracorporeal circuit composed principally of a haemodialyser 13 having a selectively permeable membrane 14 which permits the dialysis and ultrafiltration of the blood, preferably two blood circulation pumps 15 and 16, various accessories of which only the main ones are shown, and connecting lines between these various devices. As accessories, there will only be mentioned here a pulsation-absorbing device 17, preferably used singly or in duplicate, immediately adjacent to the haemodialyser, especially when the latter is of the hollow fibre type; a bubble remover 18 incorporating a filter (not shown) and an air bubble detector 19 which has overriding control over the automatic closing of an obstructing clamp 20 situated in the return line which connects the bubble remover directly to the single needle 12.

The dialysis liquid circuit can be of any known type, in particular of the type open over a discharge to the drain, or closed on itself with or without recirculation of the dialysis liquid into the haemodialyser and/or with or without mixing of the used liquid with the fresh liquid in the reservoir 21. FIG. 1 shows such a dialysis liquid circuit symbolically. The reservoir 21 incorporates a water inlet 22 and a dialysis concentrate inlet 23 for introducing the liquid in a predetermined ratio, and also means for discharging the excess used dialysis liquid 24 and ultrafiltrate 25. A deformable diaphragm 26 can, for example, isolate the used dialysis liquid from the fresh liquid. A pump 27 generally situated downstream from the haemodialyser provides a constant circulation of the dialysis liquid, most commonly flowing in countercurrent with respect to the blood. The haemodialyser 13 is in fact divided by the membrane 14 into two compartments, the compartment 28 being a component of the extracorporeal blood circuit and the compartment 29 being a component of the dialysis liquid circuit.

The operation of this type of artificial kidney is sequential, the blood passing through the single needle 12 alternatively from the patient 11 to the haemodialyser 13 and then from the latter to the patient. The blood pumps 15, 16 hence generally operate discontinuously and out of phase with one another. The regulation of the motion of the pumps is carried out either by programming the respective periods of operation, or preferably according to the pressure of the blood between the two pumps to avoid any excessive pressure variation, for example by means of a pressure sensor placed close to the haemodialyser, and preferably in the pressure-absorbing device 17. The operation of a single blood circulation pump can be controlled in a similar manner.

All the components of the artificial kidney described in relation to FIG. 1 are well known and will hence not be described here in further detail.

Figure 2:
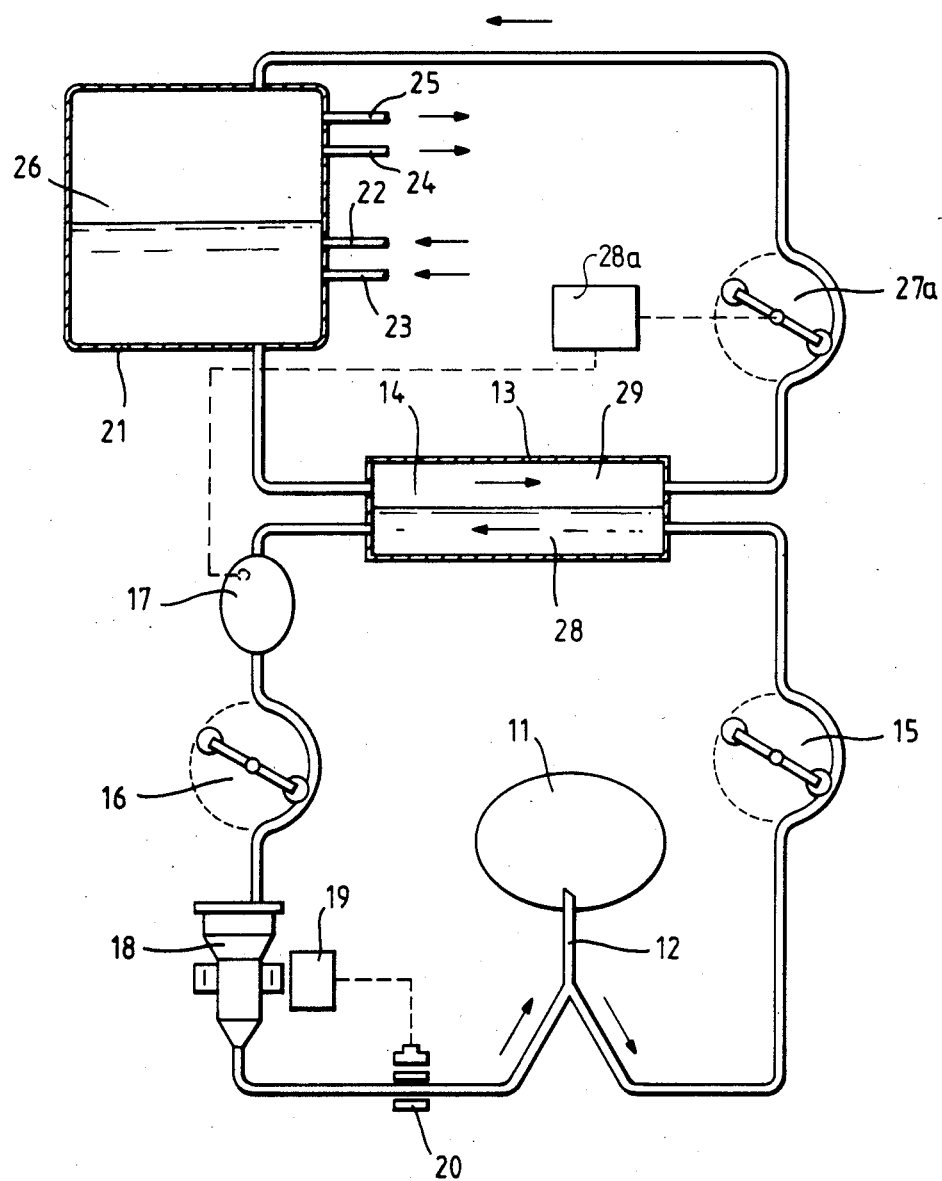

FIG. 2 shows a preferred embodiment of the present invention. The components of this single-needle artificial kidney which are equivalent to those in FIG. 1 will not be described again. Only the essential differences will be emphasised between the kidney according to the invention shown in FIGS. 2 to 5, and the known kidney shown in FIG. 1.

According to FIG. 2, the pump 27a for circulating the dialysis liquid is a multi-speed volumetric pump. This pump is driven by a motor which can drive either via a gearbox, for example having two different ratios, or via a speed variation which can intermittently drive the pump at speeds between predetermined maximum and minimum values. This motor-pump unit thus constitutes a means for intermitently modulating the flow rate of the dialysis liquid in the haemodialyser between two values, a minimum and a maximum.

The pulsation-absorbing device 17 situated in the extracorporeal blood circuit, for example immediately downstream from the haemodialyser 13 includes a blood pressure sensor (not shown) which is a member sensitive to the pulsations of blood, and which therefore at any time transmits values of this pressure at the particular moment to the servo-control device 28a. When the blood pressure values overshoot the predetermined limits, the servo-control device 28a acts automatically on the motor-pump unit 27a to switch its speed to one of the predetermined minimum or maximum speeds. Taking account of the type of haemodialyser, the pulsation-absorbing device and the deformability characteristics under the effect of the blood pressure variations in the extracorporeal blood circuit, the technician sets experimentally once and for all, and by means of a few trials, the blood pressure values measured by the pressure sensor which determine the optimum moment for triggering the change in speed of the pump 27a.

The single-needle artificial kidney according to FIG. 2 has a haemodialyser through which pass blood and dialysis liquid flowing in countercurrent and pulsed in phase. The maximum and minimum flows preferably pass simultaneously through the haemodialyser. This results in a substantially improved exchange efficiency, which is verified, in particular, in terms of the measured removal of for example urea, creatinine, uric acid and phosphates.

Figure 3:
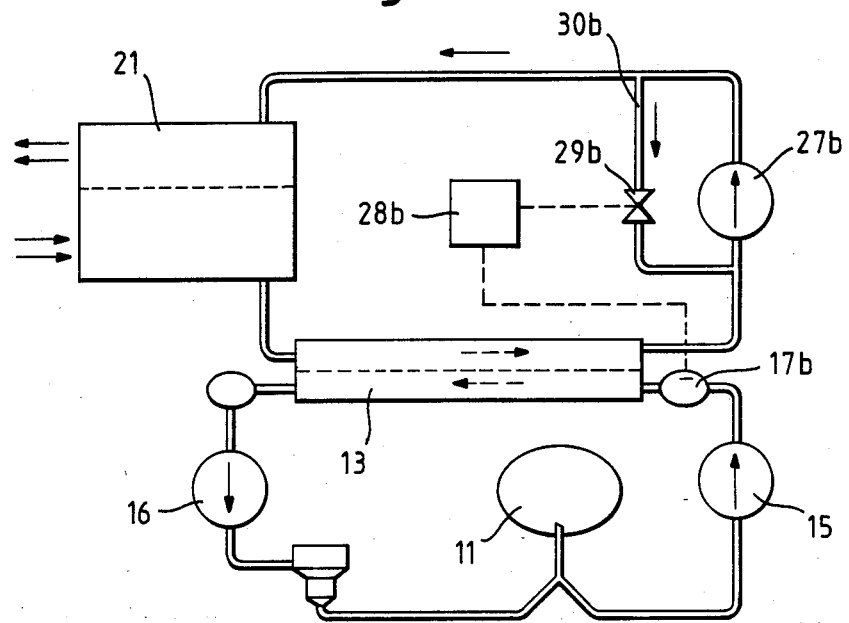
Figure 4:
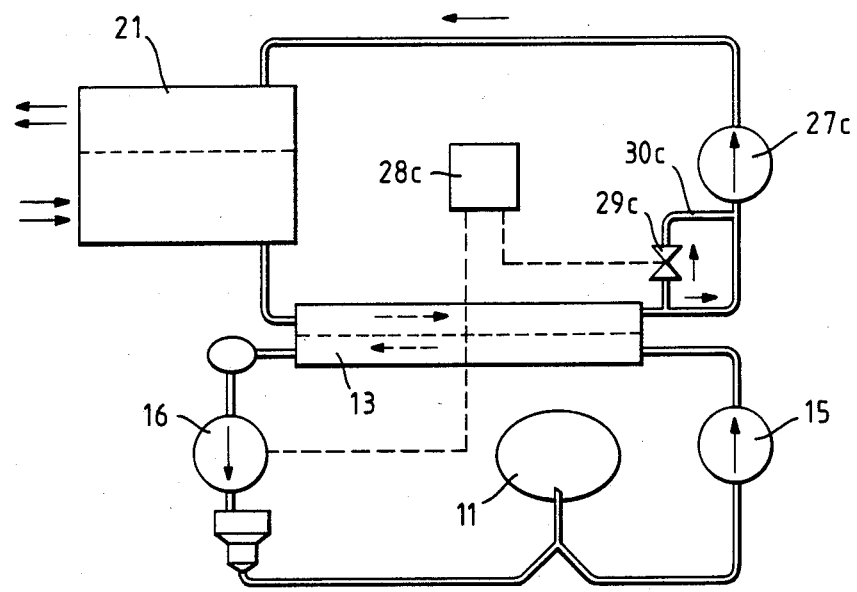

FIGS. 3 and 4 show other embodiments of the present invention which are also advantageous. The means for modulating the flow rate of dialysis liquid consist of a by-pass duct 30b, 30c arranged in parallel relative to the main pipeline, and a valve 29b, 29c having a closure member, in this by-pass duct. The open or closed position of the closure member of the valve 29b, 29c is operated by a servo-control 28b, 28c which can be actuated either by a pressure sensor mounted, for example, in the pulsation-absorbing device 17b placed immediately upstream from the haemodialyser 13, or by the starting or stopping of the blood circulation pump, for example, the downstream pump 16.

In FIG. 3, the by-pass pipeline 30 is placed in parallel with the circulation pump 27b. The latter permanently passes the used dialysis liquid from the haemodialyser 13 to the reservoir 21 according to the maximum desired flow rate. During the period when the valve 29b is open, a part of this liquid is returned from the downstream to upstream of the pump 27b, which thereby only conveys to the reservoir 21 the predetermined minimum flow. The arrows indicate the direction in which the dialysis liquid circulates. The flow rate of dialysis liquid passing through the haemodialyser is therefore intermittently modulated between the predetermined minimum and maximum values.

In FIG. 4, the by-pass pipeline 30c is placed in series with the centrifugal type circulation pump 27c for example upstream. When the valve 29c is open, the dialysis liquid is drawn in by the pump 27c simultaneously through the main pipeline and through the main pipeline and through the main pipeline and through the by-pass pipeline 30c—see arrows—and the pump 27c then supplies the predetermined maximum flow. When the valve 29c is closed, the dialysis liquid now only reaches the pump through the main pipeline, and the pump then supplies the desired minimum flow.

Figure 5:
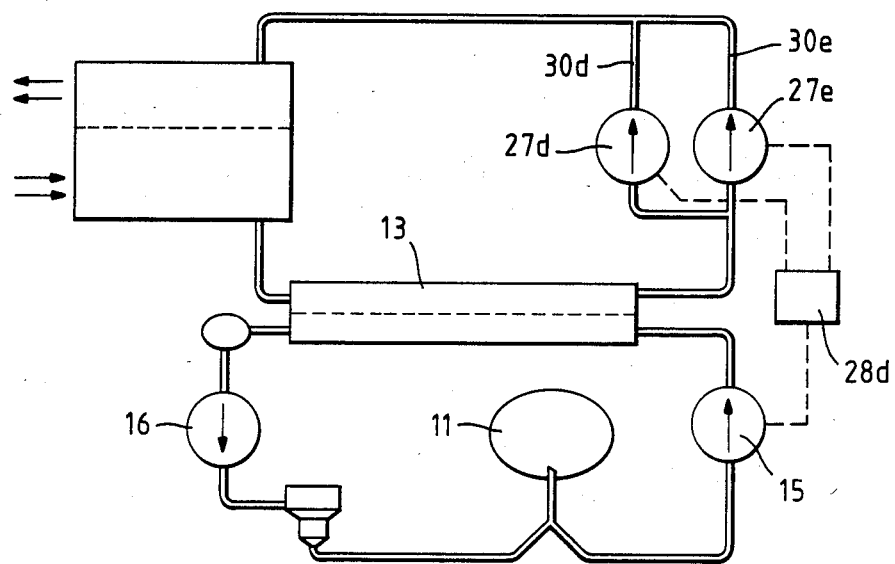

FIG. 5 shows a further embodiment of the present invention. Two pumps 27d, 27e for circulating dialysis liquid are situated in parallel on the respective pipelines 30d, 30e. Only the pump 27d has a flow capacity equal to the predetermined minimum flow rate, and only the pump 27e has a flow capacity equal to the predetermined maximum flow rate. Each of these pumps is alternatively set into motion by the servo-control 28d, which is connected, for example, to the upstream blood circulation pump 15.

As a variant, the pump has a flow capacity equal to the predetermined minimum flow rate and the pump 27e has a flow capacity equal to the difference between the predetermined maximum and minimum flow rates. The operation of the pump 27d is then continuous, while the pump 27e which alone is operated by the servo-control 28d is intermittent in operation.

The present invention can be used with any known type of haemodialyser, for example of the plate, hollow fibre or coil type. The extracorporeal blood circuit can incorporate one or, preferably, two circulation pumps. Furthermore, this circuit may or may not incorporate pulsation-absorbing devices of any known type, situated at one or more points of the extracorporeal blood circuit.

It is within the capacity of the technician to combine together or organise the different possibilities mentioned here for modulating the flow rate of the dialysis liquid, or to develop equivalent possibilities. For example, it is possible to actuate intermittently a valve placed in the dialysis liquid circuit, between a fully open and a partially open position of the valve closure member. The sequential control of the flow rate of dialysis liquid in phase with the pulsations of the blood in a single-needle artificial kidney can obviously be the subject of numerous further embodiments within the capacity of the technician, without departing from the scope of the present invention.

I claim:

1. An artificial kidney which includes a haemodialyser (13) a semi-permeable membrane (14) which can effect dialysis and ultrafiltration of the blood, said diaphragm dividing said haemodialyser into first and second compartments (28), (29) an extracorporeal blood circuit including said first compartment (28), a blood circulation pump (15, 16) and a single needle (12) for insertion into the patient (11), a dialysis liquid circuit including said second compartment (29) and a dialysis liquid pump (27), characterized in that said dialysis liquid circuit includes means for enabling simultaneous pulsing of both blood and dialysis liquid in the haemodialyser of said single-needle artificial kidney, sufficient to provide the high efficiencies otherwise obtained with conventional double-needle artificial kidneys, including means (27a, 27b, 27c, 27d, 27e) for periodically modulating the flow rate of said dialysis liquid in the said haemodialyser (13) between minimum and maximum values, a sensor (17) sensitive to the pulsation of the blood in said extracorporeal blood circuit at a frequency below 1 hertz, and a servo-control (28a, 28b, 28c, 28d) operable in response to said sensor to control said means for periodically modulating the flow of dialysis liquid as a function of said pulsations of the blood at frequencies below 1 hertz.

2. An artificial kidney according to claim 1, characterized in that the said means for periodically modulating the flow (27a, 27b, 27c, 27d, 27e) of the dialysis liquid, are synchronized through the servo-control (28a, 28b, 28c, 28d) to a sensor (15, 16, 17) which is sensitive to the pulsations of the blood, whereby the flow rates of blood and dialysis liquid are simultaneously at the maximum and minimum values in the haemodialyser (13).

3. An artificial kidney according to claim 1 or 2, characterised in that said means for periodically modulating the flow rate of dialysis liquid act at a frequency which is substantially constant and between 0.1 and 1 hertz.

4. An artificial kidney according to any one of the preceding claims, characterised in that the flow rate of the dialysis liquid is modulated between 100 and 1000 ml per min.

5. An artificial kidney according to any one of the preceding claim, characterised in that said sensor is situated in the extracorporeal blood circuit at a point (17) close to said haemodialyser (13).

6. An artificial kidney according to any one of the preceding claim, characterized in that said means for modulating the flow rate of the dialysis liquid comprise a multi-speed volumetric circulation pump (27a) operated intermittently by the said servo-control (28a).

7. An artificial kidney according to any one of claims 1 to 4 characterized in that said sensor is a blood circulation pump (15, 16) in said extracorporeal blood circuit.

8. An artificial kidney according to any one of claims 1 to 7, characterized in that said means for periodically modulating the flow rate of the dialysis liquid comprise a by-pass duct (30b), (30c) arranged in parallel with respect to said dialysis liquid circuit, a valve (29b, 29c) provided with a closure member said valve being situated in said by-pass duct, the position of said closure member being operated intermittently by said servo-control (28b, 28c).

9. An artificial kidney according to any one of claims 1 to 7, characterized in that said means for periodically modulating the flow rate of the dialysis liquid comprises two circulation pumps (27d, 27e) arranged in parallel at least one of which is periodically operated by said servo-control (28d).

* * * * *